(12) United States Patent
Pohl et al.

(10) Patent No.: US 6,682,733 B1
(45) Date of Patent: Jan. 27, 2004

(54) FIBRINOLYTIC ENZYMES

(75) Inventors: Gunnar Pohl, Sundyberg (SE); Lennart Hansson, Lidingö (SE); Björn Löwenadler, Täby (SE)

(73) Assignee: Roche Diagnostics, GmbH, Mannheim (DE)

( * ) Notice: Subject to any disclaimer, the term of this patent is extended or adjusted under 35 U.S.C. 154(b) by 1799 days.

(21) Appl. No.: 08/653,104

(22) Filed: May 24, 1996

Related U.S. Application Data (63) Continuation of application No. 08/263,397, filed on Jun. 21, 1994, now abandoned, which is a continuation of application No. 07/863,540, filed on Apr. 6, 1992, now abandoned, which is a continuation of application No. 07/207,856, filed on Jun. 17, 1988, now abandoned.

(30) Foreign Application Priority Data

Jun. 18, 1987 (SE) .............................................. 8702562

(51) Int. Cl.$^7$ ............................................... A61K 38/48
(52) U.S. Cl. ..................... 424/94.64; 435/219; 435/226
(58) Field of Search .............................. 435/226, 172.3, 435/212, 219; 424/94.63, 94.64

(56) References Cited

U.S. PATENT DOCUMENTS

| | | | | |
|---|---|---|---|---|
| 5,073,494 A | * | 12/1991 | Heyneker et al. | 435/226 |
| 5,106,741 A | * | 4/1992 | Marotti et al. | 435/226 |
| 5,202,121 A | * | 4/1993 | Pohl et al. | 424/94.64 |

FOREIGN PATENT DOCUMENTS

| | | | | |
|---|---|---|---|---|
| EP | 178105 | * | 4/1986 | C12N/15/00 |
| EP | 196920 | * | 10/1986 | C12N/9/72 |
| EP | 225286 | * | 6/1987 | C12N/15/00 |

OTHER PUBLICATIONS van Zonneveld, A. et al. (1986) FNAS 83, 4670–4674.*
Burck et al, *Journal of Cellular Biochem.*, Supp. 13E, p. 198, (1989).
van Zonneveld, *The Journal of Biological Chem.*, vol. 261, p. 14214 (1986).
Burck et al, *The Journal of Biological Chem.*, vol. 265, p. 5170 (1990).
Collen et al, *Blood*, vol. 71, No. 1, pp. 216–219, (1988).
Hotchkiss et al, *Thrombosis and Haemostasis*, vol. 60, pp. 255–261 (1988).
Tanswell et al, *Fibrinolysis*, vol. 3, pp. 79–84, (1989).
Wu et al, *Journal of Cardiovascular Pharmacology*, vol 16, pp. 197–203 (1990).
Pohl et al, *Fibrinolysis*, vol. 5, pp. 17–29, (1991).
Wikström et al, *Fibrinolysis*, vol. 5, 31–41, (1991).

* cited by examiner

*Primary Examiner*—Nashaat T. Nashed
(74) *Attorney, Agent, or Firm*—Fulbright & Jaworski (57) ABSTRACT

A fibrinolytically active plasminogen activator of the tissue type, wherein the growth factor (G) domain has been deleted, and wherein also the K1 domain has been deleted and additionally has been modified in one or more of the following sites or region: the sites of amino acid residues 177, 184, 277 and 448 and the F domain, the F domain modification if present being a deletion of part or all of said domain;

DNA-sequence comprising a nucleotide sequence coding for said plasminogen activator;

expression vector which in a transformed host cell can express said DNA-sequence;

host cell transformed using such vector;

pharmaceutical composition comprising the fibrinolytically active plasminogen activator;

plasminogen activator for use in treating thrombotic disease;

a process for the manufacture of such fibrinolytically active plasminogen activator;

a process for the treatment of thrombotic disorder; and a process of localizing thrombi while using such plasminogen activator.

16 Claims, 5 Drawing Sheets

FIG. 1A

```
                                                                  CC-101
GAGAGCTGAGATCCTACTGGAGTCCAGGGCTGGAGAGAAAACCTCTGCGAGGAAAGGGAA     -41
GGAGCAAGCCGTGAATTTAAGGGACGCTGTGAAGCAATCATGGATGCAATGAAGAGAGGG      21
                                        MetAspAlaMetLysArgGly
                                                         -35
CTCTGCTGTGTGCTGCTGCTGTGTGGAGCAGTCTTCGTTTCGCCCAGCCAGGAAATCCAT      81
LeuCysCysValLeuLeuLeuCysGlyAlaValPheValSerProSerGlnGluIleHis

GCCCGATTCAGAAGAGGAGCCAGATCTTACCAAGTGATCTGCAGAGATGAAAAAACGCAG     141
AlaArgPheArgArgGlyAlaArgSerTyrGlnValIleCysArgAspGluLysThrGln
                            -1 +1                          10
ATGATATACCAGCAACATCAGTCATGGCTGCGCCCTGTGCTCAGAAGCAACCGGGTGGAA     201
MetIleTyrGlnGlnHisGlnSerTrpLeuArgProValLeuArgSerAsnArgValGlu
                   20                                    30
TATTGCTGGTGCAACAGTGGCAGGGCACAGTGCCACTCAGTGCCTGTCAAAAGTTGCAGC     261
TyrCysTrpCysAsnSerGlyArgAlaGlnCysHisSerValProValLyeSerCysSer
          40                                      50
GAGCCAAGGTGTTTCAACGGGGGCACCTGCCAGCAGGCCCTGTACTTCTCAGATTTCGTG     321
GluProArgCysPheAsnGlyGlyThrCysGlnGlnAlaLeuTyrPheSerAspPheVas
                60                              70
TGCCAGTGCCCCGAAGGATTTGCTGGGAAGTGCTGTGAAATAGATACCAGGGCCACGTGC     381
CysGlnCysProGluGlyPheAlaGlyLysCysCysGluIleAspThrArgAlaThrCys
                      80                         90
TACGAGGACCAGGGCATCAGCTACAGGGGCACGTGGAGCACAGCGGAGAGTGGCGCCGAG     441
TyrGluAspGlnGlyIleSerTyrArgGlyThrTcpSerThrAlaGluSerGlyAlaGlu
                            100                      110
TGCACCAACTGGAACAGCAGCGCGTTGGCCCAGAAGCCCTACAGCGGGCGGAGGCCAGAC     501
CysThrAsnTrpAsnSerSerAlaLeuAlaGlnLysProTyrSerGlyArgArgProAsp
                              120                       130
GCCATCAGGCTGGGCCTGGGGAACCACAACTACTGCAGAAACCCAGATCGAGACTCAAAG     561
AleIleArgLeuGlyLeuGlyAsnHisAsnTyrCysArgAsnProAspArgAspSerLys
                              140                       150
CCCTGGTGCTACGTCTTTAAGGCGGGGAAGTACAGCTCAGAGTTCTGCAGCACCCCTGCC     621
ProTrpCysTyrValPheLysAlaGlyLysTyrSerSerGluPheCysSerThrProAla
                              160                       170
TGCTCTGAGGGAAACAGTGACTGCTACTTTGGGAATGGGTCAGCCTACCGTGGCACGCAC     681
CysSerGluGlyAsnSerAspCysTyrPheGlyAsnGlySerAlaTyrArgGlyThrHis
                              180                       190
AGCCTCACCGAGTCGGGTGCCTCCTGCCTCCCGTGGAATTCCATGATCCTGATAGGCAAG     741
SerLeuThrGluSerGlyAlaSerCysLeuProTrpAsnSerMetIleLeuIleGlyLys
                              200                       210
GTTTACACAGCACAGAACCCCAGTGCCCAGGCACTGGGCCTGGGCAAACATAATTACTGC     801
ValTyrThrAlaGlnAsnProSerAlaGlnAlaLeuGlyLeuGlyLysHisAsnTyrCys
                              220                       230
CGGAATCCTGATGGGGATGCCAAGCCCTGGTCCACGTGCTGAAGAACCGCAGGCTGACG     861
ArgAsnProAspGIyAspAlaLysProTrpCysHisValLeuLysAsnArgArgLeuThr
                              240                       250
TGGGAGTACTGTGATGTGCCCTCCTGCTCCACCTGCGGCCTGAGACAGTACAGCCAGCCT     921
TrpGluTyrCysAspValProSerCysSerThrCysGlyLeuArgGlnTyrSerGlnPro
                              260                       270
CAGTTTCGCATCAAAGGAGGGCTCTTCGCCGACATCGCCTCCCACCCCTGGCAGGCTGCC     981
GlnPheArgIleLysGlyGlyLeuPheAlaAspIleAlaSerHisProTrpGlnAlaAla
                              280                       290
ATCTTTGCCAAGCACAGGAGGTCGCCCGGAGAGCGGTTCCTGTGCGGGGGCATACTCATC    1041
IlePheAlaLysHisArgArgSerProGlyGluArgPheLeuCynGlyGlyIleLeuIle
                              300                       310
AGCTCCTGCTGGATTCTCTCTGCCGCCCACTGCTTCCAGGAGAGGTTTCCGCCCCACCAC    1101
SerSerCysTrpIleLeuSerAlaAlaHisCysPheGlnGluArgPheProProHisHis
```

FIG. 1B

```
                   320                          330
CTGACGGTGATCTTGGGCAGAACATACCGGGTGGTCCCTGGCGAGGAGGAGCAGAAATTT  1161
LeuThrValIleLeuGlyArgThrTyrArgValValProGlyGluGluGluGlnLysPhe
                   340                          350
GAAGTCGAAAAATACATTGTCEEEAAGGAATTCGATGATGACACTTACGACAATGACATT  1221
GluValGluLysTyrIleValEEELysGluPheAspAspAspThrTyrAspAsnAspIle
                   360                          370
GCGCTGCTGCAGCTGAAATCGGATTCGTCCCGCTGTGCCCAGGAGAGCAGCTGGGTCCGC  1281
AlaLeuLeuGlnLeuLysSerAspSerSerArgCysAlaGlnGluSerSerValValArg
                   380                          390
ACTGTGTGCCTTCCCCCGGCGGACCTGCAGCTGCCGGACTGGACGGAGTGTGAGCTCTCC  1341
ThrValCysLeuProProAlaAspLeuGlnLeuProAspTrpThrGluCysGluLeuSer
                   400                          410
GGCTACGGCAAGCATGAGGCCTTGTCTCCTTTCTATTCGGAGCGGCTGAAGGAGGCTCAT  1401
GlyTyrGlyLysHisGluAlaLeuSerProPheTyrSerGluArgLeuLysGluAlaHis
                   420                          430
GTCAGACTGTACCCATCCAGCCGCTGCACATCACAACATTTACTTAACAGAACAGTCACC  1461
ValArgLeuTyrProSerSerArgCysThrSerGlnHisLeuLeuAsnArgThrValThr
                   440                          450
GACAACATGCTGTGTGCTGGAGACACTCGGAGCGGCGGGCCCCAGGCAAACTTGCACGAC  1521
AspAsnMetLeuCysAlaGlyAspThrArgSerGlyGlyProGlnAlaAsnLeuHisAsp
                   460                          470
GCCTGCCAGGGCGATTCGGGAGGCCCCCTGGTGTGTCTGAACGATGGCCGCATGACTTTG  1581
AlaCysGlnGlyAspSerGlyGlyProLeuValCysLeuAsnAspGlyArgMetThrLeu
                   480                          490
GTGGGCATCATCAGCTGGGGCCTGGGCTGTGGACAGAAGGATGTCCCGGGTGTGTACACA  1641
ValGlyIleIleSerTrpGlyLeuGlyCysGlyGlnLysAspValProGlyValTyrThr
                   500                          510
AAGGTTACCAACTACCTAGACTGGATTCGTGACAACATGCGACCGTGACCAGGAACACCC  1701
LysValThrAsnTyrLeuAspTrpIleArgAspAsnMetArgPro
                   520
GACTCCTCAAAAGCAAATGAGATCCCGCCTCTTCTTCTTCAGAAGACACTGCAAAGGCGC  1761
AGTGCTTCTCTACAGACTTCTCCAGACCCACCACACCGCAGAAGCGGGAGCAGACCCTAC  1821
AGGAGAGGGAAGAGTGCATTTTCCCAGATACTTCCCATTTTGGAAGTTTTCAGGACTTGG  1881
TCTGATTTCAGGATACTCTGTCAGATGGGAAGACATGAATGCACACTAGCCTCTCCAGGA  1941
ATGCCTCCTCCCTGGGCAGAAAGTGGCCATGCCACCCTGTTTTCAGCTAAAGCCCAACCT  2001
CCTGACCTGTCACCGTGAGCAGCTTTGGAAACAGGACCACAAAAATGAAAGCATGTCTCA  2061
ATAGTAAAAGATAACAAGATCTTTCAGGAAAGACGGATTGCATTAGAAATAGACAGTATA  2121
TTTATAGTCACAAGAGCCCAGCAGGGCTCAAAGTTGGGGCAGGCTGGCTGGCCCGTCATG  2181
TTCCTCAAAAGCACCCTTGACGTCAAGTCTCCTTCCCCTTTCCCCACTCCCTGGCTCTCA  2241
GAAGGTATTCCTTTTGTGTACAGTGTGTAAAGTGTAAATCCTTTTTCTTTATAAACTTTA  2301
GAGTAGCATGAGAGAATTGTATCATTTGAACAACTAGGCTTCAGCATATTTATAGCAATC  2361
CATGTTAGTTTTTACTTTCTGTTGCCACAACCCTGTTTTATACTGTACTTAATAAATTCA  2421
GATATATTTTTTCACAGTTTTTTCCAAAAAAAAAAAA
```

FIBRINOLYTIC ENZYMES

This application is a continuation, of application Ser. No. 08/263,397, filed Jun. 21, 1994, now abandoned, which is a continuation of Ser. No. 07/863,540 filed Apr. 6, 1992, abandoned, which is a continuation of Ser. No. 07/207,856, filed Jun. 17, 1988, abandoned.

FIELD OF INVENTION

The present invention relates to fibrinolytically active plasminogen activators of the tissue type, DNA-sequences coding for same, pharmaceutical compositions containing same and processes for their production.

In particular, this invention relates to tissue-type plasminogen activators (t-PA) which have been modified in such a way that a; the uptake of the enzyme by the liver is reduced and b; the enzyme is essentially resistant to inactivation by plasma inhibitors. As a result the modified t-PA:s covered by this invention are characterized by a longer biological half-life than the t-PA preparations (native or recombinant) previously used.

Another aspect of this invention relates to the expression of t-PA, native or modified, in eucaryotic cells. More particularly, the invention relates to specific DNA sequences containing mRNA processing signals and which induce high production of recombinant proteins in heterologous cells.

BACKGROUND ART

Vascular disorders such as myocardial infarction, pulmonary embolism, stroke, deep vein thrombosis, periferal arterial thrombosis and other vascular thromboses are caused by partial or total occlusion of a blood vessel by blood clots. The clot which consists of a fibrin network can be dissolved by firinolytic enzymes. Plasmin is one such fibrinolytic enzyme which is present in the blood as an inactive proenzyme, plasminogen. Plasminogen activators convert plasminogen to plasmin, which in turn degrades the fibrin to soluble fragments. Thus, plasminogen activators can be use to induce thrombolysis.

The tissue plasminogen activator is regarded to be highly suitable for thromblytic treatments since it is a physiological compound with affinity for fibrin, and which activates plasminogen efficiently only in the presence of fibrin (Camiolo et al, *Proc. Soc. Exp. Biol. Med.*, 138, pp. 277–280, 1971 and Ranby, M., *Biochem. Biophys. Acta*, 704, pp. 461–469, 1982). Thus, it is a clot selective fibrinolytic agent suitable for intravenous administration. Other plasminogen activators such as streptokinase, a bacterial protein, or urokinase, isolated from urine, activates plasminogen but are not clot selective. As a result circulating plasmin is generated which may cause a haemorrhagic potential because the circulating plasmin degrades clotting factors such as fibrinogen, factor VIII and factor V.

Clinical studies have demonstrated the thrombolytic effectiveness of t-PA for treatment of acute myocardial infarction. (The TIMI Study Group, *N. Enql. J. Med.*, 312, p. 932, 1985 and Verstraete et al, *Lancet*, 1, pp. 842–847, 1985). However, due to the rapid clearance of t-PA by the liver (Korninger et al, *Thromb. Haemostas.*, 46, pp. 658–661, 1981) high doses 50–90 mg had to be given as a continuous infusion in order to induce efficient thrombolysis. The biological half-life of t-PA in man is only a few minutes Tiefenbrunn et al, *Circulation*, 71, pp. 110–116, 1985), and only a small fraction of the activator will actually reach the clot. Another factor which further reduces the amount of t-PA available for clot lysis is the reaction with plasma inhibitors. It has been shown that t-PA forms complexes with a number of plasma protease inhibitors including the recently discovered plasminogen activator inhibitors of endothelial and placental type. (Rijken et al, *J. Lab. Clin. Med.*, 101, pp. 285–294, 1983; Wiman et al, *J. Biol. Chem.*, 259, pp. 3644–3647, 1984; and Lecander et al, *British Journal of Haemathology*, 57, pp. 407–412, 1984).

The modifications of t-PA according to the present invention solves both the problem of the short biological half-life due to the liver clearance and the sensitivity to inactivation by plasma inhibitors.

The DNA sequences containing the information for t-PA and derivatives thereof can be introduced into appropriate vectors for expression in eucaryotic cells. The fibrinolytic activity produced by the transiently transfected or stably transformed host cells may be measured by using standard assays for plasminogen activators. The eucaryotic expression vectors described herein may be constructed by techniques well known by those skilled in the art, using components such as replicons, enhancers, promoters etc from natural sources or chemically synthesized by conventional procedures.

Established cell lines, as well as normal diploid cells, are suitable as hosts. A large number of different cell lines are usable for expression of t-PA or derivatives thereof. For example, different hamster cell lines such as $CHOd^-$, CHOK1 and BHK, monkey cell lines such as CV-1 and COS, mouse cell lines such as C127 and 3T3, as well as human cell lines may be used. Other hosts such as insect cells as well as transgenic organisms may also be used for the production of t-PA or t-PA derivatives.

After introduction into a suitable host cell, the t-PA coding DNA sequences may be contained and propagated either as stably integrated into the host cell genome or in extrachromosomal form.

The sequences comprising the t-PA gene is preferentially present in the cells in multiple copies. Different strategies for amplification of t-PA gene copy number may be exploited. For stable integration of the vector DNA into the host cells chromosomal DNA, and for the subsequent amplification of the integrated vector DNA, an amplifiable selectable gene is included in the t-PA expression vector. Chinese hamster ovary cells (CHO) are presently preferred together with the dihydrofolate reductase (DHFR) gene as an amplifiable selectable marker gene. (Kaufman et al, *Mol. Cell. Biol.*, 7, pp. 1750–1759, 1985).

Another amplification system is based on the use of papilloma virus DNA, especially bovine papilloma virus 1 (BPV). All or part of the virus genome is used to obtain stable transformation of mouse cells such as C127 or 3T3. The viral genome contains information for the maintenance of the vector DNA as a stable extrachromosomal element at a high copy number Sambrook et al, *Embo J.*, 1, pp. 91–103, 1985).

In the eucaryotic host-vector systems discussed above, the expression of t-PA molecules or variants of the t-PA molecule is influenced by different upstream and downstream regulating DNA elements.

Figure 3:
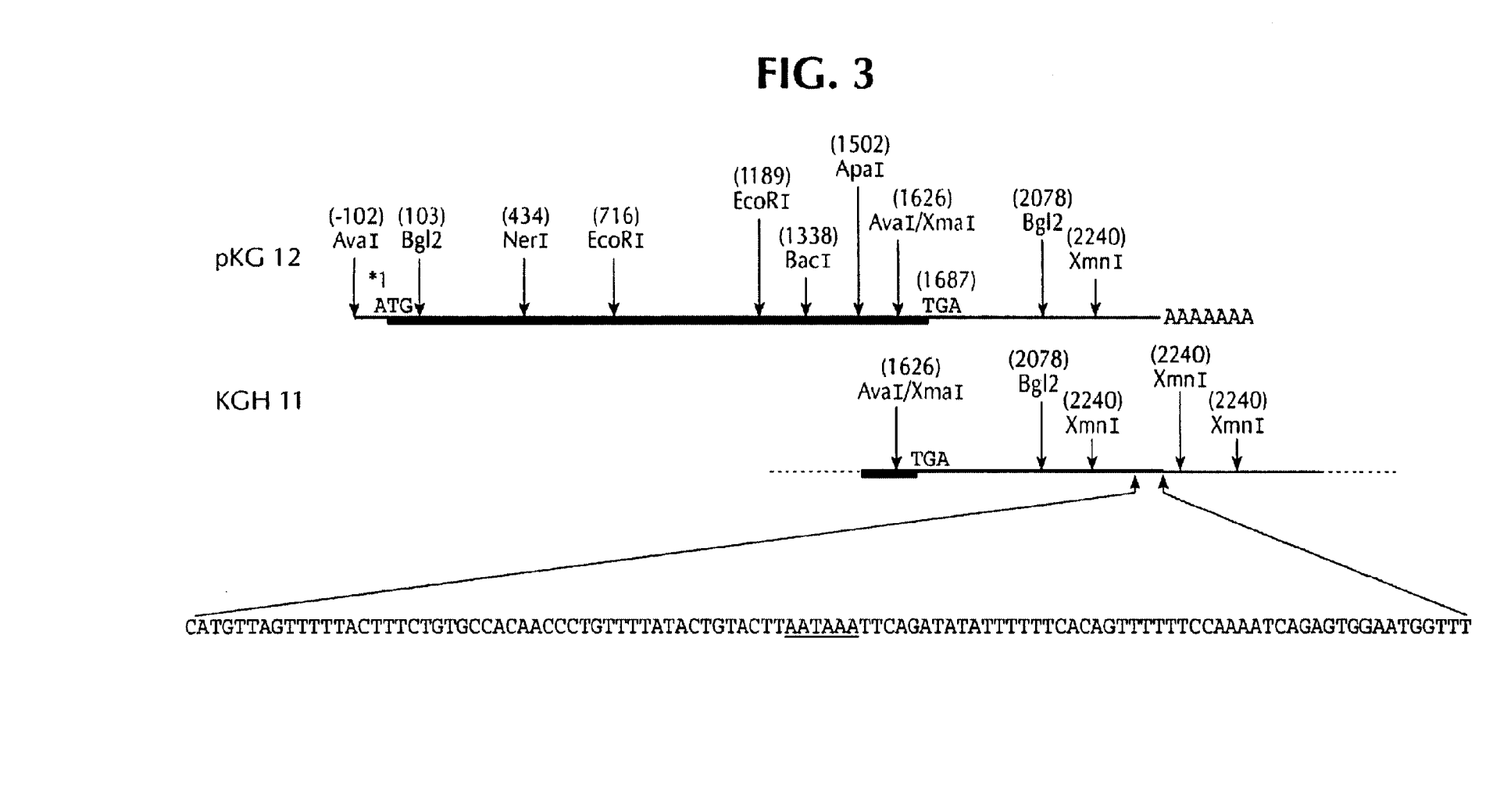
FIG. 3: Schematic representation of the human genomic DNA fragment, included in clone KGH11, with reference to the nucleotide numbering in pKG12. The sequence shown, represent part of the last exon, carrying the poly A signal as well as 3' flanking genomic DNA.

We have isolated and characterized a DNA fragment (KGH 11) from a human genomic library, which contains downstream processing signals such as polyadenylation signal etc from the human t-PA gene. The appropriate DNA fragment contains a part of the sequence in the last exon of the human t-PA gene. Since this segment also is represented in the cDNA it provides the possibility to use a unique restriction enzyme site in the overlapping region as a fusion site for ligation of the two elements (FIG. 3) For the eucaryotic expression systems analyzed, the production levels from this homologous construction were significantly higher than from expression vector constructions which are identical except for the processing signals downstream of the t-PA gene.

Recombinant DNA and other biotechnological techniques have been employed in order to obtain efficient production of t-PA for treatment of vascular diseases. Promising clinical studies were first performed with t-PA isolated from human melanoma cells. (Coken D, *Circulation*, 72, pp. 18–20, 1985).

Amino acid sequence analysis of the human melanoma t-PA (Wallén et al, *Eur. J. Biochem.*, 132, pp. 681–686, 1983) provided the necessary information for the synthesis of DNA probes which were used for the isolation of, first a partial cDNA (Edlund et al, *Proc. Natl. Acad. Sci. USA*, 80, pp. 349–352, 1983), and subsequently a complete cDNA coding for the entire protein (FIG. 1).

Other examples where cDNA:s coding for t-PA have been isolated and where attempts have been made to produce t-PA in heterologous cells are referred to in European patent applications 93619 and 178105. See also reference (Pennica et al, *Nature*, 301, pp. 214–221, 1983).

Amino acid sequence determinations of various preparations of human t-PA have revealed differences in the N-terminal starting position. Due to differences in processing of the nascent molecule L,S, and U-forms of polypeptides are produced (Pohl et al, *FEBS Lett.*, 168, pp. 657–663, 1985). The L-form is characterized by having glycine as the N-terminal residue. The N-terminal residue of the S-form and the U-form is serine and valine respectively. The numbering system for the amino acid sequence of t-PA used herein is based on the S-form where the N-terminal serine is numbered 1. As a consequence the L-form N-terminal glycine is at position −3, and the U-form N-terminal valine is at position 4. It is understood that the tissue plasminogen activator modified in accordance with the present invention encompasses all such variant forms.

Different parts of the t-PA molecule show homologies with parts of other proteins. As disussed in (Patthy, L, *Cell*, 41, pp. 657–663, 1985) the native t-PA molecule consists of five structural domains which have been termed "finger domain" (F), "growth factor domain" (G), "Kringle domain" (K1 and K2 for Kringle 1 and Kringle 2) and "protease domain" (P) respectively. Thus native t-PA can schematically be described by the formula:

*F-G-K1-K2-P*

The exon/intron junctions of the human t-PA gene have been determined (Ny et al, *Proc. Natl. Acad. Sci. USA*, 81, pp. 5355–5359, 1984), and the positions of these junctions can be used to define the boundries between the different domains in the amino acid sequence. Thus, the F domain consists of amino acid residues 4–50, the G domain consists of residues 51–87, the K1 domain consists of residues 88–176, and the K2 domain consists of residues 177–262. Following the K2 domain is a short connecting peptide consisting of the residues 263–274. The P domain is coded for by 5 exons and is contained within the amino acid sequence of residues 275–527 (Pohl et al, *Biochemistry*, 23, pp. 3701–3707, 1984). Human t-PA is synthesized as a single-chain 19 polypeptide but can be converted into a two-chain form where the two chains are connected through a disulfide bond. The heavy chain (residues 1–274) consists of the F, G, K1 and K2 domains together with a short connecting peptide, and the light chain (residues 275–527) consists of the P domain.

The fact that native, single-chain t-PA express activity with synthetic, low molecular weight, substrates and is inhibited by protease inhibitors (Ranby et al, *Thromb. Res.*, 27, pp. 175–183, 1982) indicate that single-chain t-PA has significant enzymatic activity. In this respect, t-PA is different from other single-chain forms of serine proteases which have essentially no activity with synthetic substrates and does not react with inhibitors. It has been suggested (Wallén et al, *Eur. J. Biochem.*, 132, pp. 681–686, 1983) that the enzymatic activity of the single-chain t-PA may be caused by the presence of a certain lysine residue (position 277 in the t-PA molecule). In all other serine proteases the corresponding position (i.e. position 2 after the activation cleavage site) is occupied by a small hydrofobic residue.

Attempts have been made to apply recombinant DNA techniques for the production of mutated forms of t-PA where the above mentioned lysine residue is exchanged for isoleucine (see International patent applicaton PCT/US85/01613). However, this modification is not expected to reduce the rapid uptake of t-PA by the liver since it has been shown that the rapid clearance is mediated by structures in the enzymatically inactive heavy chain of the molecule. (Rijken, D. C. and Emeis, J. J., *Biochem. J.*, 238, pp. 643–646, 1986).

SUMMARY OF THE INVENTION

The main object of the present invention is to provide for fibrinolytically active plasminogen activators of the tissue type which have longer biological half-life in vivo. Another object of the invention is to provide activators which are less sensitive to inhibition by plasma inhibitors as compared with native human t-PA.

These and other objects of the invention which will be clear from the following disclosure are obtained by a fibrinolytically active plasminogen activator of the tissue type, wherein, in addition to the growth factor (G) domain, also the K1 domain has been deleted. Additionally the plasminogen activator of the invention has been modified in one or more of the following sites or region: the sites Of amino acid residues 177, 184, 277 and 448, and the F domain, if modified, being deleted in part or all of it.

It is preferred that the F domain, optionally, has been deleted and the 184 site has been modofied to prevent glycosylation thereat. It is particularly preferred that both sites 184 and 448 have been modified to provide glycosylation at said sites.

In this disclosure, when referring to modification of glycosylation sites 184 and 448, the modification is such that no glycosylation occurs. Thus, the site in question is modified so as to prevent N-glycosylation by modifying the N-glycosylation consensus sequence.

In a particularly preferred embodiment of the invention the F domain has been deleted altogether and the amino acid sites 184 and 448 have been modified to prevent glycosylation at said sites.

In such plasminogen activator it is preferred that the additional modification has been made at the site of amino acid residue 277, and such modification can be in the form of change to an amino acid residue which in its side chain does not exhibit a positive charge. An example of such modification is substituting a valine residue for the lysine residue at the 277 site.

In another preferred embodiment of the invention the additional modification has been made in the K1 domain, either as the only modification of the molecule in addition to the modification of the growth factor domain or in combination with the modification of the site of amino acid residue 277.

In yet another embodiment of the present invention modification of the molecule has been made at the site of amino acid residue 184, whereby N-glycosylation at said site, which occurs in normal t-PA, is no longer achievable. In a such modification at the 184 site the asparagine residue thereof can be replaced by a glutamine residue.

In addition to the said modifications at amino acid sites 184 and 277 it is also preferred to modify the K1 domain, optionally in combination with a modification to the F domain.

According to the present invention all such modifications to the different domains can be constituted by deletion or part of all of the respective domains.

The invention also covers a DNA-sequence comprising a nucleotide sequence encoding a fibrinolytically active plasminogen activator as described above. In addition, the invention comprises a replicable expression vector capable of expressing such a DNA-sequence. Furthermore, the invention includes host cells transformed with such replicable expression vector.

As indicated earlier in this disclosure the modified fibrinolytically active plasminogen activators according to the present invention displays a longer biological half-life as compared to native t-PA and is therefore particularly useful in pharmaceutical compositions and methods for the treatment of thrombotic diseases, such as vascular disorders.

The modified t-PA according to the present invention may be formulated using known methods for the manufacture of pharmaceutically useful compositions. Accordingly, the present invention also includes a pharmaceutical composition comprising a therapeutically effective amount of the modified t-PA in admixture with pharmaceutically acceptable carrier. The resulting compositions will provide an amount of modified t-PA effective in a patient to provide for treatment of thrombotic diseases, for example to dissolve blood clots.

Various dosage forms can be manufactured to enable administration of such pharmaceutical compositions. Thus, for example parenteral administration can be used for patients suffering from cardiovascular disorders. The dosage and frequence of administration will be selected according to the situation at hand. Because of the fact that the modified t-PA according to the present invention has been found to possess longer half-life than native t-PA the dosage can be significantly reduced compared to that presently used in therapy with prior art t-PA. Thus, quite generally, in the treatment of a patient for a thrombotic disorder there will be administered a daily dose of up to say about 1 mg/kg of body weight. Such administration can take place either by injection or by infusion.

Compositions for intravenous administration may take the form of solutions of the modified t-PA in an isotonic aqueous solution in sterile state. Such solution may contain a solubilizing agent to maintain the t-PA in solution.

According to another aspect of the invention there is provided a method of treating thrombotic disorders, which comprises administering to a patient suffering from such disorder an effective amount of the plasminogen activator according to the present invention.

In another aspect of this invention, these modified t-PA molecules which have an increased biological half-life compared with the native t-PA and have retained fibrin affinity, may be used for the in vivo localization of thrombi. The enzyme is preferably made inactive either by chemical modifications of the active site amino acid residues or by modifications of the DNA sequence coding for these residues. A number of well known methods exist for the chemical inactivation of serine proteases with agents such as diisopropylfluorophosphate (DFP), phenylmethylsulfonylfluoride (PMSF), N-p-tosyl-L-lysylchloromethane (TLCK) or peptide chloromethyl ketones such as H-D-Phe-Gly-ArgCH$_2$Cl. Inactivations by genetic modifications may be performed by using site specific mutagenesis (as in example 2) and thereby change the DNA sequence coding for any of the active site residues. Preferably, the serine residue which corresponds to Ser-478 in the native, full sized, t-PA is changed to alanine.

The invention also covers DNA-sequences comprising a nucleotide sequence encoding a modified plasminogen activator according to the invention.

The invention also includes the preferred use of a DNA fragment containing the downstream mRNA processing signals provided from the human t-PA gene for the expression of human proteins in mammalian cells. The DNA fragment is characterized by the nucleotide sequence and restriction enzyme cleavage sites shown in FIG. 3.

Furthermore, the invention provides for a replicable expression vector capable of expressing, in a transformant host cell, such a DNA-sequence. In addition, the invention includes host cells transformed with such replicable expression vector.

According to yet another aspect of the invention there is provided a process for producing a modified plasminogen activator according to the invention, such process comprising:

a) preparing a replicable expression vector capable of expressing the DNA-sequence encoding such plasminogen activator;

b) transforming a host cell culture using the vector resulting from step a) to form redombinant host cells;

c) culturing said recombinant host cells under conditions permitting expression of the plasminogen activator encoding DNA-sequence to produce said plasminogen activator;

d) recovering the resulting plasminogen activator.

In such process eucaryotic host cells may be used.

By way of example, one compound of this invention differs from the native human t-PA by lacking the growth factor domain and the first Kringle domain. The amino acid residues from Pro-47 to Glu-175 of the native t-PA are deleted and Val-46 is directly followed by Gly-176. An other difference between this exemplary compound and the native t-PA molecule is that the N-glycosylation site in the second Kringle domain (present at Asn-184 in the native molecule) is made unavailable for glycosylation by the conversation of this asparagine residue to glutamine. The lysine residue at the position which corresponds to Lys-277 in the native t-PA molecule is changed to valine. The compound modified as above is denoted FK2(Gln)P(Val). In an other exemplary compound the residues from Cys-6 to Cys-173 of the native t-PA molecule are deleted, and here Ile-5 in the amino acid sequence is followed by Ser-174. The residues corresponding to Asn-184 and Lys-277 in the native molecule are modified in the same way as in the first compound. This second compound is denoted K2(Gln)P(Val). In addition, both FK2(Gln)P(Val) and K2(Gln)P(Val) are mutated to substitute the Asn residue at position 177 with Ser.

These exemplary compounds are schematically depicted in Table 1.

TABLE 1

| Compound | residues deleted | residues changed |
|---|---|---|
| FK2(Gln)P(Val) | 47-175 | Asn-177->Ser |
| | | Asn-184->Gln |
| | | Lys-277->Val |
| K2(Gln)P(Val) | 6-173 | Asn-177->Ser |
| | | Asn-184->Gln |
| | | lys-277->Val |

The numbers given for the residues refer to the native human t-PA sequence (see FIG. 1.)

The modifications of human t-PA according to the present invention is preferably a combination of modifications or a deletion of the growth factor domain, removal of at least one glycosylation site and modification of the second residue in the protease domain (Lys) into an amino acid residue which does not exhibit a positive charge in its side chain.

These fibrinolytically active modified t-PA molecules have longer biological half-life in the blood stream and are less sensitive to inactivation by complex formation with inhibitors than the native, unmodified, t-PA (natural or recombinant). Efficient thrombolysis may be obtained with comparatively lower doses of these mutant forms of t-PA than what is presently used for the unmodified t-PA.

While not wanting to be bound by theory we speculate that smaller molecules such as the modified t-PA:s may diffuse faster into the clot and thereby induce thrombolysis more efficiently than the unmodified full sized t-PA. Our results also indicate that these smaller t-PA molecules are expressed more efficiently by eucaryotic cells. Also potentially important for large scale production is that the single-chain form of the modified molecules will not react, or react more slowly than unmodified t-PA, with plasma inhibitors. This may increase the yield of fibrinolytically active molecules from tissue cultures, since in most cases the media have to be supplemented with serum which contain protease inhibitors. It has been reported that a significant part of the secreted unmodified t-PA is complexed to inhibitors derived from foetal calf serum (Schleuning W.-D., Abstract No. 82 of the VIII:th International Congress on Fibrinolysis, Vienna, 1986).

These modified fibrinolytic enzymes may be produced by means of recombinant DNA techniques. The DNA coding for the modified molecules may be constructed by digesting full length t-PA cDNA with suitable restriction enzymes, utilize techniques such as site directed mutagenesis and/or chemical synthesis of DNA fragments. These methods are well known by those who are ordinarily skilled in the art of recombinant DNA.

The DNA coding for the modified fibrinolytic molecules may be introduced into appropriate vectors for expression in eucaryotic or procaryotic cells.

Purification of the molecules may be conducted by procedures developed and known for native human t-PA with appropriate modifications. Proper purification procedures may be developed by persons ordinarily skilled in the art of protein purification.

By using a transcriptional unit which consists of an enhancer element as well as a promoter element upstream of the coding sequence for native or modified human t-PA fused to human t-PA downstream processing signals, high level expression were obtained in all eucaryotic cell systems analyzed, e.g. mouse cells such as C127, NIH 3T3, Swiss 3T3, hamster cells such as CHOd⁻, CHOK1, HAK, RS 1610, monkey cells such as CV-1, COS-1, COS-7. The expression levels were substantially higher by the use of homologous coding and downstream processing units, compared with using downstream processing signals from non-human eucaryotic genes or from genes of viral origin. The t-PA expression sequence is with respect to the sequence in the last exon and further downstream identical to the sequence for this region found in the human genome. This region is characterized by the nucleotide sequence and restriction enzyme cleavage sites indicated in FIG. 3.

This improved homologous unit is obtained by fusion of the element providing mRNA processing signals to a corresponding site in the last exon region of the cDNA.

TURNOVER STUDIES IN RABBITS

Native and modified t-PA was injected as an intravenous bolus dose of 10–30 ug. From a cannula in the ear artery, frequent blood samples were collected and mixed with a 10% sodium citrate solution. After centrifugation the plasma samples were assayed for recombinant t-PA with an enzyme linked immunosorbent assay (ELISA) utilizing polyclonal antibodies raised against human melanoma t-PA.

DEPOSITS

Microorganisms, recombinant DNA molecules and the modified t-PA DNA coding sequences of this invention as well as starting materials useful in preparing them have been deposited in the culture collection of "Deutsche Sammlung von Mikroorganismen", Grisebachstrasse 8, D-3400 G ÖTTINGEN, Germany on Jun. 16, 1987 and have been identified there as:

A: *E.coli* JM83 (pKGE22) accession number: DMS 4142

B: *E.coli* HB 101 (pKGE81) accession number: DMS 4143

C: *E.coli* HB 101 (pKGE83) accession number: DSM 4144

D: *E.coli* HB 101 (pKGE105) accession number: DSM 4145

E: *E.coli* HB 101 (pKGE114) accession number: DSM 4146

The invention will be further understood with reference to the following illustrative embodiments, which are purely exemplary and should not be taken as limiting the true scope of the present invention as described in the claims.

This exemplification is made with reference to the appended drawings wherein:

FIG. 1: Nucleotide sequence and the deduced amino acid sequence of the full length human t-PA cDNA.

EXAMPLE 1

CLONING OF THE GENE ENCODING HUMAN TISSUE PLASMINOGEN ACTIVATOR (t-PA)

Cell Culture

Bowes melanoma cells, a transformed human cell line which constitutively produce high levels of t-PA, were cultured in glass roller bottled at +37° C. in Eagles minimal essential medium (EMEM) supplemented with 1% non essential amino acids (Flow), glutamine (2 mM), penicillin (50 IU/ml), streptomycin (50 ug/ml), Hepes (20 mM, pH 7.2) and 10% foetal calf serum.

Messenger RNA Preparation

Confluent cultures of melanoma cells were harvested by trypsination. After washing in ice cold phosphate buffered saline pH 7.2, the cells were recovered by centrifugation. Cell pellets were lysed in 4M GuSCN, and total RNA was then selectively precipated from a GuHCl solution by ethanol. Messenger RNA was purified from the total RNA preparation by chromatography on oligo-dT cellulose. The poly-$A^+$ mRNA obtained was size fractionated on a sucrose gradient, consisting of 10–30% sucrose in 50 mM LiCl, 20 mM Tris-HCl, 1 mM EDTA-Li, 1% LiDS and with a pH of 7.8.

Preparation of cDNA Bank From Melanoma Cell mRNA

Sucrose fractions corresponding to 23 S were shown to be enriched in t-PA mRNA by dot blot hybridization. 5 ug mRNA from this enriched fraction was used to construct a cDNA library essentially as described by Okayama & Berg (Okayama & Berg, *Mol. Cell. Biol.*, 3, pp. 280–289) with the modifications detailed in (Hedén et al, *FEBS Lett.*, 194, pp. 327–32, 1986). The cDNA containing plasmid pT4 prepared by the disclosed method was used to transform *E.coli* 5K. The gene bank obtained consisted of approximately $5 \times 10^4$ independent clones.

Screening for t-PA Sequence Contaig Clones

The isolated partial t-PA cDNA clone (Edlund et al, *Proc. Natl. Acad. Sci. USA*, 80, pp. 349–352, 1983), was used to screen the gene library for t-PA sequence containing clones. A 476 bp Eco RI fragment of the cDNA clone was nicktranslated with $^{32}$P-dCTP to a specific activity of about $5 \times 10^7$ CPM/ug using a commercial nicktranslation kit (NEN). Bacterial colonies were transferred to PALL filters by the method suggested by the manufacturer and were hybridized to the nicktranslated DNA probe in 50% formamide, 5×SSC, 250 ug/ml yeast RNA at 37° C. over night. After washing in 3 changes of 2×SSC at ambient temperature, the filters were dried and exposed on X-ray film.

Sequencing of t-PA cDNA

One clone, designated pKG12, was identified after autoradiography. Digestion with the restriction enzymes Kpn I and Pst I showed that pKG12 contained an insert of about 2.5 kb. The insert was subcloned into M13 mp10 and mp11 (Messing, J., *Methods Enzymol.*, 101, pp. 20–78, 1983) and DNA sequence analysis was performed using the dideoxy chain termination method (Sanger et al, *PNAS*, 74, pp. 5463–5467, 1977). Clone pKG12 was shown to comprise the whole coding region for human t-PA as well as 102 bp 5' flanking, 760 bp 3' flanking DNA and a poly A tract. The complete DNA sequence of pKG12 is shown in FIG. 1.

Subcloning of t-PA for Eucaryotic Expression

Figure 2:
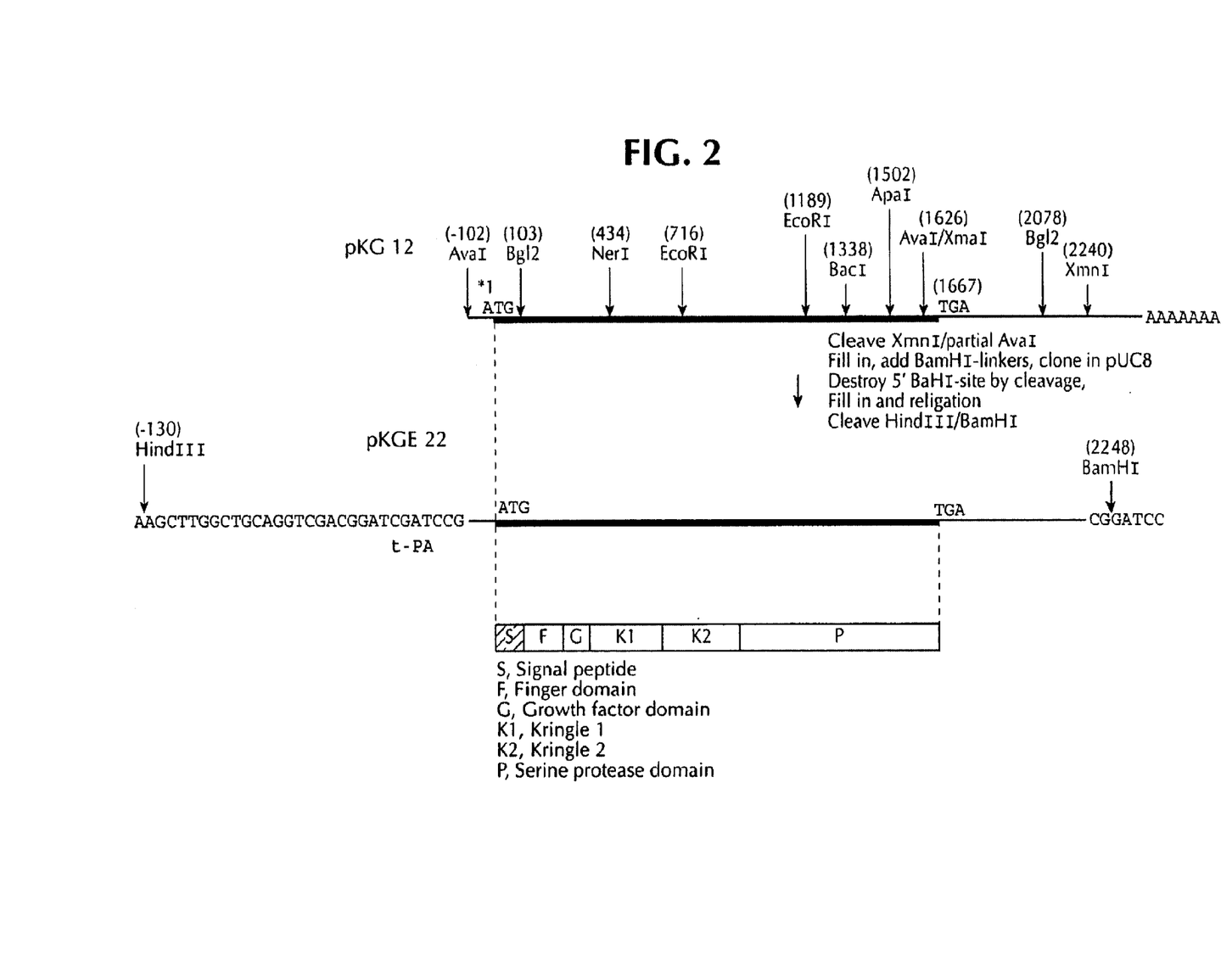
FIG. 2: Schematic representation of the relationship between the full length t-PA cDNA in vector pKG12 and the t-PA cDNA modified for eucaryotic expression (pKGE22) as described in example 1, and the t-PA protein with its different domains indicated below.

As seen in FIG. 2, the whole coding sequence and all of the 5' noncoding region and 559 bp of the 3' noncoding DNA is contained within a 2350 partial Ava I/Xmn I fragment.

To obtain this fragment, 25 ug pKG12 was cleaved to completion with 30 units Xmn I overnight at 37° C. Ava I (9 units) was added and the cleavage continued for another 1 h and 20 min at 37° C. The various cleavage products obtained were separated in a 0.6% low gelling temperature agarose gel (LGT-agarose, BioRad). The 2350 bp band was excised and melted at 68° C., followed by phenol extraction and ethanol precipitation. The purified fragment was made blunt ended by a fill-in reaction using the Klenow fragment of DNA polymerase in the presence of dNTP:s. Bam HI linkers (5'-CGCGGATCCGCG-3') were added to the fragment using T4 DNA ligase. After subsequent cleavage with Bam HI and removal of excess Bam HI linker-fragments by 0.7% LGT-agarose electrophoresis, the t-PA fragment was ligated to Bam HI cleaved pUC8. The resulting plasmid, denoted pKGE22 contains most of the t-PA cDNA within a Hind III/Bam HI fragment. The sequence downstream of the Xmn I site, harboring the putative polyadenylation signal AATAAA has been removed.

The ligation mixture was used to transform competent *E.coli* JM83 cells. White colonies were selected on agar plates containing 50 ug/ml ampicillin and 25 ul/plate of 2% X-gal in dimethylformamide.

EXAMPLE 2

CONSTRUCTION OF K2(Gln)P(Val)

The strategy used to construct the gene encoding a t-PA molecule lacking the F, G, and K1 domain was first to remove the 613 bp restriction fragment spanning from Bgl II at position 103 to the Eco RI site at position 716 and then to fuse the K2 domain directly to the signal peptide using an oligonucleotide linker.

By removal to the 613 bp internal Bgl II/Eco RI fragment, the region encoding the whole F, G, and K1 domains are deleted. A linker fragment was used to restore the deleted part of the K2 domain along with the 5 N-terminal amino acid residues of the mature, processed t-PA. Furthermore the glycosylation site Asn184 was changed to Gln and the asparagine residue at position 177 was substituted with a serine reside.

The linker fragment that allowed fusion between the signal peptide and the K2 domain was constructed by synthesis of two complementary 116 bp oligonucleotides using the phosphoamidite method (Elmblad et al, *Nucl. Acids Res.*, 10, pp. 3291–3301, 1982).

50 pmoles each of the synthesized 116-mers were phosphorylated using T4 Polynucleotide kinase (New England Biolabs) as described by Maniatis et al. (Maniatis et al, *Molecular cloning—A Laboratory Manual*, Cold Spring Harbor Laboratory, 1982). The two strands were annealed by heating to 70° C. for 5 min, after which the temperature was allowed to decrease to 20° C. over a period of 60 min. 5 pmoles of the double stranded linker was ligated to 0.1 pmole of M13 mp8, digested with Eco RI and Hind III, using standard ligation conditions (Maniatis et al, *Molecular cloning—A Laboratory Manual*, Cold Spring Harbor Laboratory, 1982). The ligation mixture was subsequently used to transform competent *E.coli* JM 103. Recombinants were selected as white plaques on X-gal plates. Single stranded phage DNA was isolated and sequenced by the dideoxy method [26] using a 17-mer M13 universal sequencing primer 3'-GTAAAACGACGGCCAT-5'. The double stranded replicative form (RF) from one clone having the correct sequence, was pepared, and used for further construction work.

Double stranded DNA from the M13 clone above was digested to completion with Bgl II and Eco RI. The 110 bp fragment obtained, was recovered from a 1.2% LGT agarose gel (BioRad, USA). The plasmid pKGE22 was partially digested with Bgl II and Eco RI, and the various cleavage products were separated in a 0.6% LGT agarose gel. A4381 bp fragment lacking the internal region of t-PA from Bgl II at position 103 to Eco RI at position 716 was isolated. The 110 bp Bgl II/Eco RI oligonucleotide linker was ligated to the 4381 bp partial Bgl II/Eco RI digest of pKGE22 using T4 DNA ligase, thus yielding plasmid pKGEP75. The ligation mixture was used to transform competent E.coli HB101 cells. Plasmid DNA from clones appearing on selective plates containing Amp (50 ug/ml) was prepared.

Next, the lysine residue corresponding to the amino acid at position 277 in the unmodified t-PA sequence was changed to valine by oligonucleotide directed mutagenesis.

The plasmid pKGEP75 was digested with Sal I/Sac I and a 0.9 kb fragment was recovered from an 0.9% LGT agarose gel. This fragment, which contains the DNA sequence coding for amino acid 277, was cloned into M13 mp19. Single stranded DNA of an M13 clone harboring the 0.9 kb Sal I/Sac I insert was prepared. This single stranded DNA was hybridized to a synthetic oligonucleotide (5'-GCCCTCCCACGATGCGAAA-3'). Annealing was made in 1×TM buffer (10 mM Tris-HCl, 10 mM MgCl 2, pH 8.0) for 5 min at 70° C. After 1 h when the temperature reached 20° C., 1 ul 10×TM buffer, 1 ul 10 mM ATP, 1 ul 20 mM dNTP, 1 ul 100 mM DTT, 5 units Klenow fragment and 12 units T4 DNA ligase was added. The extension/ligation reaction was performed at 15° C. for 4 h.

The resulting couble stranded DNA was directly used to transform competent JM 103 cells, and 200 plaques were hybridized to the mismatch primer labelled with $^{32}$P at the 5' end. One plaque, giving a strong hybridization signal after washing at 50° C., was purified and the double standed replicative form was prepared.

The 900 bp Sal I/Sac I fragment containing the Lys Val modification was recovered after cleavage with Sal I and Sac I followed by 0.9% LGT agarose gel electrophoresis. This fragment was cloned into Sal I/Sac I digested pKGEP75, thus obtaining plasmid pKGE114.

Plasmid pKGE114 encodes the exemplary compound which is denoted K2(Gln)P(Val).

EXAMPLE 3

CONSTRUCTION OF FK2(Gln)P(Val)

In plasmid pKGEP114 the K2 domain is preceded by a Basm HI site. This site was used to introduce the region coding for the F domain immediately in front of the K2 domain.

By site directed mutagenesis a Bam HI site was created at the junction between the F and the G domains in the t-PA cDNA sequence. Plasmid pKGE22 was digested with Sal I and Eco RI to completion. A 800 bp fragment spanning the signal sequence and the F, G and K1 domains was recovered after LGT agarose electrophoresis, and subdloned into M13 mp19. The single stranded form of this M13 clone served as template for the in vitro mutagenesis. A synthetic 24 bp oligonucleotide mismatch primer (5'-GCAACTTTTGGATCCCACTGAGTG-3') was used to convert amino acid residue 47 and 48 from Pro-Val to Gly-Ser and thereby creating a Bam HI site at the interface between the G and the K1 domains. One plaque which gave a strong hybridization signal with the $^{32}$P labelled 24 bp mismatch primer, was purified and double stranded DNA was prepared.

The double stranded DNA was digested with Sal I and Bam HI, and the fragment containing the 5' non translated region as well as the signal sequence and the F domain was recovered from 0.8% LGT agarose.

To obtain plasmid pKGEP115, encoding the exemplary compound FK2(Gln)P(Val), plasmid pKGFP114 was digested with Sal I to completion followed by partial LBasm HI cleavage. The fragment corresponding to the pUC8 vector along with the t-PA gene lacking the 5' non translated region and the signal sequence was excised and ligated to the Sal I/Bam HI fragment containing the signal sequence and the F domain.

EXAMPLE 4

EXPRESSION OF FIBRINOLYTICALLY ACTIVE t-PA AND t-PA DERIVATIVES IN EUCARYOTIC CELLS.

The expression units controlling the modified cDNA:s prepared as in examples 2 and 3 and the full length cDNA as in example 1 with appropriate polarity ligated to a DNA fragment containing enhancer and promoter sequences and the genomic fragment from the down-stream region of the human t-PA gene were introduced into several vectors for expression in different cell systems.

The eucaryotic expressions vectors were introduced into the cells by conventional transfection methods. Transient expression or expression in selected clones of host cells were assayed with an enzyme linked immunosorbent assay (ELISA) and fibrinolytic activity was assayed on plasminogen containing fibrin plates.

A) Transient Expression in C0S-7 Monkey Cells

An expression vector containing the SV 40 late promoter, a polyadenylation signal and the small t intron from SV 40, and a bacterial replicon and selective marker (pML2d), was constructed. The basic feature of the COS expression vector is that cDNA sequences can be inserted between the SV 40 late promoter and the 3' polyadenylation-signal sequence using Sal I/Bgl II compatible cohesive ends. Full length t-PA cDNA, K2(Gln)P(Val) and FK2(Gln)P(Val) coding sequences was obtained on Sal I/Bam HI fragments from vectors pKGE22, pKGEP114 and pKGEP115 respectively. These fragments were ligated to the Sal I/Bgl II digested COS expression vector yielding the vectors pKGE74, pKE114 and pKGE115.

Figure 4:
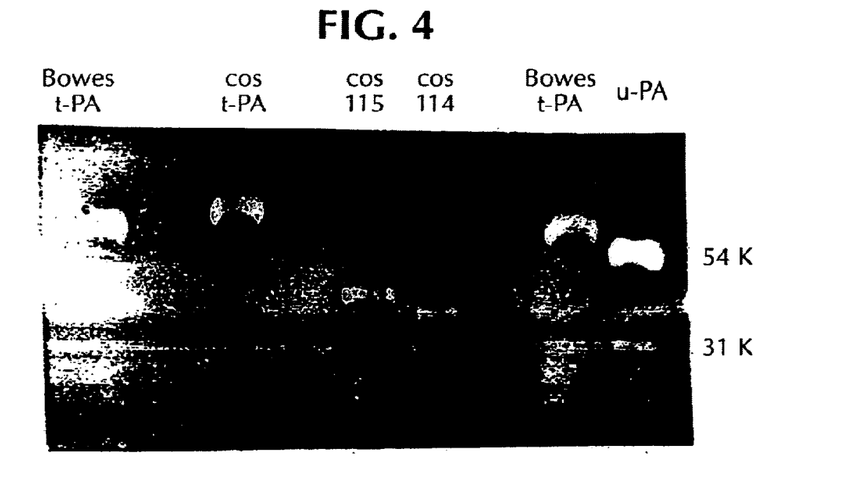
FIG. 4: Fibrin autography after SDS/polyacrylamide gel electrophoresis of full sized human t-PA and modified forms of t-PA produced in COS cells.
Figure 5:
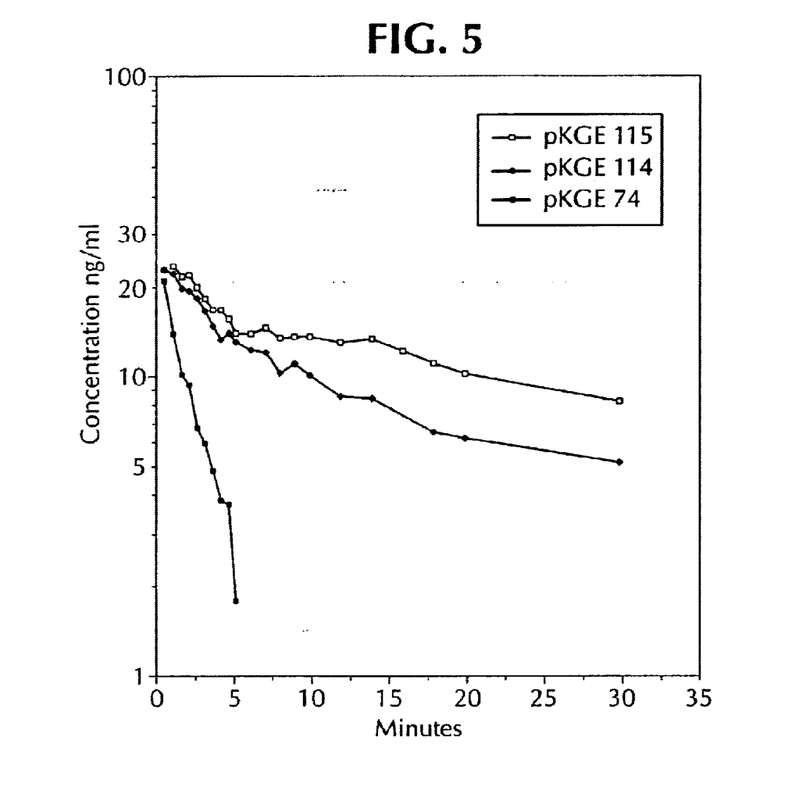
FIG. 5: Elimination of native full sized human t-PA (pKGE74) and modified forms of t-PA (pKGE114, 115) from rabbit plasma.

These expression plasmids were introduced into COS-7 cells via the DEAE-Dextran transfection protocol (Sompayrac & Danna, *J. Virol. Methods*, 5, 335–341, 1982 (DEAE-Dextran transfection)). Medium was harvested 48 and 72 h post transfection and assayed for antigen and fibrinolytic activity. Further characterization was performed by SDS/polyacrylamide gel electrophoresis followed by fibrin autography (see FIG. 4).

B) Stable Expression in C127 Mouse Cells

For production of modified or native t-PA in stably transformed mouse cells, vectors which are capable of high copy number extrachromosomal replication were used. The expression vector pKGE83, in which the t-PA gene is under the control of the mouse metallothionein promoter (mMT-1) and with polyadenylation signal and other downstream signals derived from a human genomic fragment which covers the exon 14 of the t-PA gene was constructed. The eucaryotic replication origin, plasmid maintenance sequences and transformation of host cells are effected by bovine papilloma virus (BPV).

The starting plasmids are pMTtPA, containing the t-PA gene between Hind III and Bam HI sites in pUC8, the mMT-1 promoter element and the SV 40 small t intron and polyadenylation signal and the pML2d-BPV variant, pKGE50.

The plasmids, pMTPA and pKGE50 were digested with Bam HI and Sal I. From pMTtPA a 3.9 kb fragment containing t-PA and control elements was isolated and ligated to a Bam HI/Sal I fragment containing the entire BPV genome and pML2d sequences to yield the plasmid pKGE61.

In the next step the plasmid pKGE27, which contains a genomic fragment covering more than the exon 14 region of the human t-PA gene, was digested with Apa I and Sal I. This fragment containing processing signals such as the polyadenylation signal sequence was inserted into pKGE61 which had been digested with Apa I and Sal I. The resulting plasmid was denoted pKGE83.

The plasmid pKGE113 which is similar to pKGE83 but contains the cDNA modified as in example 2, was constructed by the ligation of a 10.2 kb Apa I Bam HI fragment derived from pKGE83. The plasmid contains the entire BPV-1 genome, the pML2d sequences, the distal portion of the t-PA gene, a 0.7 kb Bam HI Sal I fragment containing mMT-1 promoter element and a Sal I Apa I fragment including the cDNA modifications.

These host vector systems are capable of high expression of intact or modified t-PA. Table 2 summarizes expression levels obtained for C127 cells after transfection with different plasmids. The amount of ELISA-detectable protein as well as fibrinolytic activity was higher in the clones producing modified t-PA than those transfected with the corresponding vector coding for the full length molecule. It can also be concluded that expression levels are increased when the genomic fragment containing the human t-PA downstream processing signal is used.

TABLE 2

| plasmid | production (pg/cell/day) | |
|---------|---------|---------|
| | mean value | max value |
| pKGE61 | 0.5 | 4 |
| pKGE83 | 3.1 | 9 |
| pKGE113 | 6.1 | 25 |

The vectors indicated above were transfected into mouse C127 cells by use of the calcium phosphate method (Wiegler et al, *Proc. Natl. Acad. Sci. USA*, 76, pp. 1373–1376, 1979). The cells were cotransfected with the plasmid pKGE53 which contains the gene coding for neomycin resistance under the control of Harvey sarcoma virus 5' LTR (long terminal repeat). The neomycin analog G418 was added to the media (1 mg/ml), and between 40 and 100 clones were isolated after approximately 2 weeks of cultivation in G418 containing medium. The clones were grown individually and assayed for expression of t-PA antigen with an ELISA assay.

C) Stable Expression in CHO Cells

The expression vector pKGE25, contains the full length t-PA cDNA under the control of SV 40 early promoter and SV 40 processing signals, a transcription unit for DHFR driven by mouse mammary tumor virus MMTV 5' LTR and polyadenylation signals and other downstream processing signals from SV 40 and a DNA fragment containing the procaryotic replication signals from pBR 322. The vector was transfected into DHFR deficient CHO cells (Urlaub & Chasin, *Proc. Natl. Acad. Sci. USA*, 77, pp. 4216–4220, 1980) and transformants were isolated and grown in increasing concentrations of the dihydrofolate reductase inhibitor methotrexate (MTX).

Expression values obtained for one typical transformant (pKGE25 7:9) in relation to MTX amplification are shown in Table 3.

TABLE 3

| uM MTX | production (pg/cell/day) |
|--------|--------------------------|
| 0.00 | 0.05 |
| 0.02 | 0.15 |
| 0.50 | 4.7 |
| 10.0 | 9.7 |

CHOd⁻ cells were cultivated in medium F-12 containing nucleosides. After transfection the medium was changed to Eagles alpha-MEM lacking nucleosides. Surviving clones were amplified by cultivation in increasing concentrations of methotrexate. Production of t-PA antigen was analyzed with an ELISA assay.

What is claimed is:

1. Isolated, thrombolytically active protein consisting of amino acids 177–527 of wild type, human tissue type plasminogen activator, with the proviso that amino acids 184 and 448 have been modified to prevent glycosylation at said amino acids.

2. The isolated, thrombolytically active protein of claim 1, wherein amino acid 184 is Gln.

3. The isolated, thrombolytically active protein of claim 2, wherein the amino acid at position 177 has been changed from Asn to Ser, and the amino acid at position 277 has been changed from Lys to Val.

4. Composition of matter comprising a therapeutically effective amount of the isolated, thrombolytically active protein of claim 1, and a pharmaceutically acceptable carrier.

5. Composition of matter comprising a therapeutically effective amount of the isolated, thrombolytically active protein of claim 2, and a pharmaceutically acceptable carrier.

6. Composition of matter comprising a therapeutically effective amount of the isolated, thrombolytically active protein of claim 3, and a pharmaceutically acceptable carrier.

7. Method for treating a thrombolytic disorder, comprising administering to a patient in need thereof, an effective amount of the isolated, thrombolytically active protein of claim 1.

8. Method for treating a thrombolytic disorder, comprising administering to a patient in need thereof, an effective amount of the isolated, thrombolytically active protein of claim 2.

9. Method for treating a thrombolytic disorder, comprising administering to a patient in need thereof, an effective amount of the isolated, thrombolytically active protein of claim 3.

10. Method for treating a thrombolytic disorder, comprising administering to a patient in need thereof an effective amount of the composition of claim 4.

11. Method for treating a thrombolytic disorder, comprising administering to a patient in need thereof an effective amount of the composition of claim 5.

12. Method for treating a thrombolytic disorder, comprising administering to a patient in need thereof an effective amount of the composition of claim 6.

13. Isolated, thrombolytically active protein consisting of amino acids 177–527 of wild type, human tissue type plasminogen activator, with the proviso that amino acids 184 and 448 have been modified to prevent glycosylation at said amino acids, and amino acid 177 has been changed from Asn to Ser.

14. Composition of matter comprising a therapeutically effective amount of the isolated, thrombolytically active protein of claim 13, and a pharmaceutically acceptable carrier.

15. Method for treating a thrombolytic disorder, comprising administering to a patient in need thereof, an effective amount of the isolated, thrombolytically active protein of claim 13.

16. Method for treating a thrombolytic disorder, comprising administering to a patient in need thereof an effective amount of the composition of claim 14.

* * * * *